US012751788B2

(12) United States Patent
Lindenmann et al.

(10) Patent No.: US 12,751,788 B2
(45) Date of Patent: Oct. 6, 2026

(54) DEPTH STOP ADAPTER

(71) Applicant: Medos International Sarl, Le Locle (CH)

(72) Inventors: Philippe Lindenmann, Basel (CH); Jörn Richter, Kandern (DE); Daniela Hammer, Basel-Landschaft (CH)

(73) Assignee: Medos International Sarl, Le Locle (CH)

( * ) Notice: Subject to any disclaimer, the term of this patent is extended or adjusted under 35 U.S.C. 154(b) by 345 days.

(21) Appl. No.: 18/371,260

(22) Filed: Sep. 21, 2023

(65) Prior Publication Data

US 2025/0099200 A1 Mar. 27, 2025

(51) Int. Cl.
*A61B 90/00* (2016.01)
*A61B 34/30* (2016.01)

(52) U.S. Cl.
CPC .............. *A61B 90/03* (2016.02); *A61B 34/30* (2016.02); *A61B 90/06* (2016.02); *A61B 90/08* (2016.02); *A61B 2034/305* (2016.02); *A61B 2090/035* (2016.02); *A61B 2090/062* (2016.02); *A61B 2090/0807* (2016.02)

(58) Field of Classification Search
CPC ...................................................... A61B 90/03
See application file for complete search history.

(56) References Cited

U.S. PATENT DOCUMENTS

| | | | | |
|---|---|---|---|---|
| 5,409,493 | A * | 4/1995 | Greenberg | A61C 1/084 606/86 R |
| 5,520,692 | A * | 5/1996 | Ferrante | A61B 17/1677 606/88 |
| 6,887,247 | B1 | 5/2005 | Couture et al. | |
| 8,882,778 | B2 * | 11/2014 | Ranft | A61B 17/1782 606/87 |
| 10,987,116 | B2 | 4/2021 | Peterson et al. | |
| 11,103,317 | B2 | 8/2021 | Crawford et al. | |
| 2012/0123417 | A1 | 5/2012 | Smith | |
| 2016/0030076 | A1 * | 2/2016 | Faller | A61B 17/320092 606/169 |
| 2017/0056205 | A1 * | 3/2017 | Biegun | A61F 2/4637 |
| 2017/0333211 | A1 * | 11/2017 | Flakne | A61F 2/3886 |
| 2023/0017263 | A1 | 1/2023 | Gan et al. | |

* cited by examiner

*Primary Examiner* — Christian A Sevilla
(74) *Attorney, Agent, or Firm* — Flaster Greenberg P.C.

(57) ABSTRACT

A depth stop adapter may include a depth stop guide tube. The depth stop guide tube may define a hollow interior configured to receive a drill bit such that the drill bit can extend through the depth stop guide tube. The depth stop adapter may include a housing comprising a first end and a second end. There may be a first aperture configured to receive the depth stop guide tube proximate the first end. There may be a second aperture between the first aperture and the second end. A foot plate may be configured to provide a depth indication. A rod may be configured to be received by the second aperture. A distal end of the rod may be configured to attach to the foot plate. A depth control element may be configured to adjust a position of the foot plate relative to the housing.

20 Claims, 10 Drawing Sheets

DEPTH STOP ADAPTER

BACKGROUND

In a medical context, drill guides are used in surgical procedures where it is necessary to drill a hole. Drill guides are particularly useful for spinal surgery, where extreme precision is required to avoid harming the patient with a drill bit. The orientation, position, and depth of the drill bit require precision, especially in spinal surgery as the area near the spine includes nerves and sensitive tissue.

Existing solutions for drill guides may not include a depth adjustment mechanism. Alternatively, the surgeon may have difficulty in easily knowing the current depth of the drill bit. Within this context, there is a need for an improved solution for a depth stop adapter.

SUMMARY

The application is generally related to devices and methods used for handling and manipulating the depth of a drill bit, for example in a medical context, and more particularly, to manipulating the depth of a drill bit in spinal surgery.

A depth stop adapter may include a housing. The housing may include a first end and a second end. The second end may be configured to attach to a navigational array. There may be an aperture (e.g., a first aperture) proximate the first end. The aperture may be configured to receive a depth stop guide tube. The depth stop guide tube may be configured to receive a drill bit. For example, the depth stop guide tube may define a hollow interior that is configured to receive a drill bit such that the drill bit can extend through the depth stop guide tube. The aperture may be sized to accommodate different sized depth stop guide tubes. Different sized depth stop guide tubes may be used for different drill bits. The depth stop guide tube may include an inner sleeve and/or an outer sleeve. The inner sleeve may include a bottom end. The bottom end may include a beveled tip and/or a narrowed bottom aperture. Positioning of the drill bit relative to the anatomical area may be improved by the beveled tip and/or the narrowed bottom aperture.

Since a surgeon has to remain focused during surgery, it is desirable to indicate the position and depth of the drill bit, as easily as possible. Indicia may be included on the depth stop guide tube, for example on an outer surface of an outer sleeve. The indicia may include a scale with a plurality of markings. Markings may include, for example, one or more lines. Each of the plurality of markings may be associated with a depth measurement. For example, the depth measurements may be associated with a distance that the drill bit extends from the depth stop guide tube (e.g., the bottom end of the depth stop guide tube). The indicia may be on an inner surface of the depth stop guide tube, for example on an inner surface of the outer sleeve. Additionally, or alternatively, the indicia may be on an inner and/or outer surface of the inner sleeve. For example, the outer sleeve and/or inner sleeve may be transparent, and indicia may be visible when viewed from the ambient environment.

One or more of the plurality of markings may be labeled. For example, a marking may be labeled with a number. The number may be associated with the depth measurement. Additionally, or alternatively, markings may include different lengths. Each length may be associated with an increment. For example, there may be three marking lengths. A first marking length may be associated with a ten millimeter increment, a second marking length may be associated with a five millimeter increment, and/or a third marking length may be associated with a one millimeter increment. Additionally, or alternatively, one or more marking lengths may be associated with a fraction of a distance unit, for example of a standard distance unit. A standard distance unit may be a millimeter, a centimeter, an inch, or a plurality of any of these (e.g., 2 millimeters). Marking lengths may be associated with length increments. For example, a longest marking length may be associated with a largest measurement (e.g., one centimeter and/or one inch) and a smallest marking length may be associated with a smallest measurement (e.g., one millimeter, two millimeters, and/or one sixteenth inch). Intermediate measurements may be associated with corresponding marking length increments.

The housing may include an aperture (e.g., a second aperture). The aperture (e.g., second aperture) may be between the first aperture and the second end of the housing. The aperture (e.g., second aperture) may be configured to receive a rod. The rod may include a proximate end and a distal end. The rod may be configured to be attached to a foot plate. For example, the distal end of the rod may be configured to attach to the foot plate. The foot plate may be configured to provide a depth indication. For example, the foot plate may be configured to indicate the depth by pointing to the indicia on the depth stop guide tube. The foot plate may include a notch. The notch may be configured to at least partially enclose the depth stop guide tube. For example, the notch may be sized to accommodate different sized depth stop guide tubes. Different sized depth stop guide tubes may be used for different drill bits. The notch may include a bevel, which for example, may contact the depth stop guide tube. The bevel may more accurately indicate the depth, for example by pointing more accurately to the indicia. Alternatively, or additionally, an etching on the foot plate may indicate the depth. The etching may include an arrow and/or other pointer.

The depth stop adapter may include a depth control element. The depth control element may be configured to adjust a position of the foot plate relative to the housing and/or the depth stop guide tube. For example, the depth control element may include a wheel. The wheel may include tactile feedback, for example the wheel may include a textured surface. Additionally, or alternatively, the wheel may include one or more ridges. The ridges may be separated by grooves, for example with a spacing between two ridges (e.g., the spacing of one groove) being uniform for the spacing between any adjacent two ridges.

The wheel may be configured to rotate such that the foot plate position changes with rotation of the wheel. For example, the rod may be configured to contact the wheel. When the wheel rotates, the rod may concurrently rotate. Rotation of the rod may cause the foot plate to move toward or away from the housing. The rod may contact the wheel at an inner portion of the wheel. Additionally, or alternatively, the rod may contact the wheel at one or more of the grooves. The rod may be a threaded rod. For example, a thread may be one or more of helical, straight, tapered, square, V-shaped, acme, knuckle, buttress, worm, single, multi, Metric standard, British standard, and/or Unified standard.

The wheel may be laterally offset from the depth stop guide tube. For example, the wheel may be between the depth stop guide tube and the second end of the housing. This position may be a natural position for a surgeon's hand to be located during usage. For example, the surgeon may have one hand on the drill handle and the other hand on the depth stop adapter. The wheel may be positioned such that the surgeon's thumb naturally lands near a position of the wheel. This may result in easy adjustment of the depth, without the need to look (e.g., constantly look) at the wheel when changing the depth. The surgeon's other hand may also naturally land near the navigational array, where for example movement of the navigational array can be restricted by the surgeon's fingers.

The depth stop adapter may include a sensory feedback element. The sensory feedback element may be configured to produce sensory feedback. The sensory feedback may include an audible click. The sensory feedback element may be configured to connect into a slot located in the wheel. For example, the sensory feedback element may be a leaf spring, a ball bearing, a ball detent, and/or a spring element (e.g., other type of spring). The sensory feedback may be produced at least partially by the sensory feedback element. For example, the sensory feedback may include an audible click. A change in the depth (e.g., the position of the foot plate) may be associated with an audible click. Each audible click may be associated with a predetermined change in the depth (e.g., position of the foot plate). The predetermined change in the depth may be, for example, two millimeters. Each audible click and/or predetermined change in depth may be associated with a predetermined rotation of the wheel. For example, the audible click and/or predetermined change in depth may be associated with a 15 degree or 180 degree rotation of the wheel. A 15 degree or 180 degree rotation of the wheel may correspond to a standard height change of the depth stop guide (e.g., 2 mm.). The sensory feedback element may additionally, or alternatively be configured to limit rotational movement of the wheel. An amount (e.g., predetermined amount) of pressure may be needed to rotate the wheel. This pressure avoids unwanted rotation of the wheel.

The depth stop adapter may be configured to attach to a robot, for example a spinal surgery robot. The robot may be programmed to position a drill and/or the depth stop adapter, for example during surgery. The robot may include an articulating arm. An example of a robot is described in U.S. Pat. No. 10,987,116B2 entitled "Adjustable drill guides and related methods" which is hereby incorporated by reference.

Additional features and advantages are realized through the system of the present invention. Other embodiments and aspects of the disclosure are described in detail herein. For a better understanding of the disclosure with advantages and features, refer to the description and to the drawings.

BRIEF DESCRIPTION OF THE DRAWINGS

Many aspects of the disclosure can be better understood with reference to the following drawings. The components in the drawings are not necessarily to scale, with emphasis being placed upon clearly illustrating the principles of the present disclosure. Moreover, in the drawings, like reference numerals designate corresponding parts throughout the several views. Furthermore, each drawing contained in this provisional application includes at least a brief description thereon and associated text labels further describing associated details.

DETAILED DESCRIPTION

Figure 1:
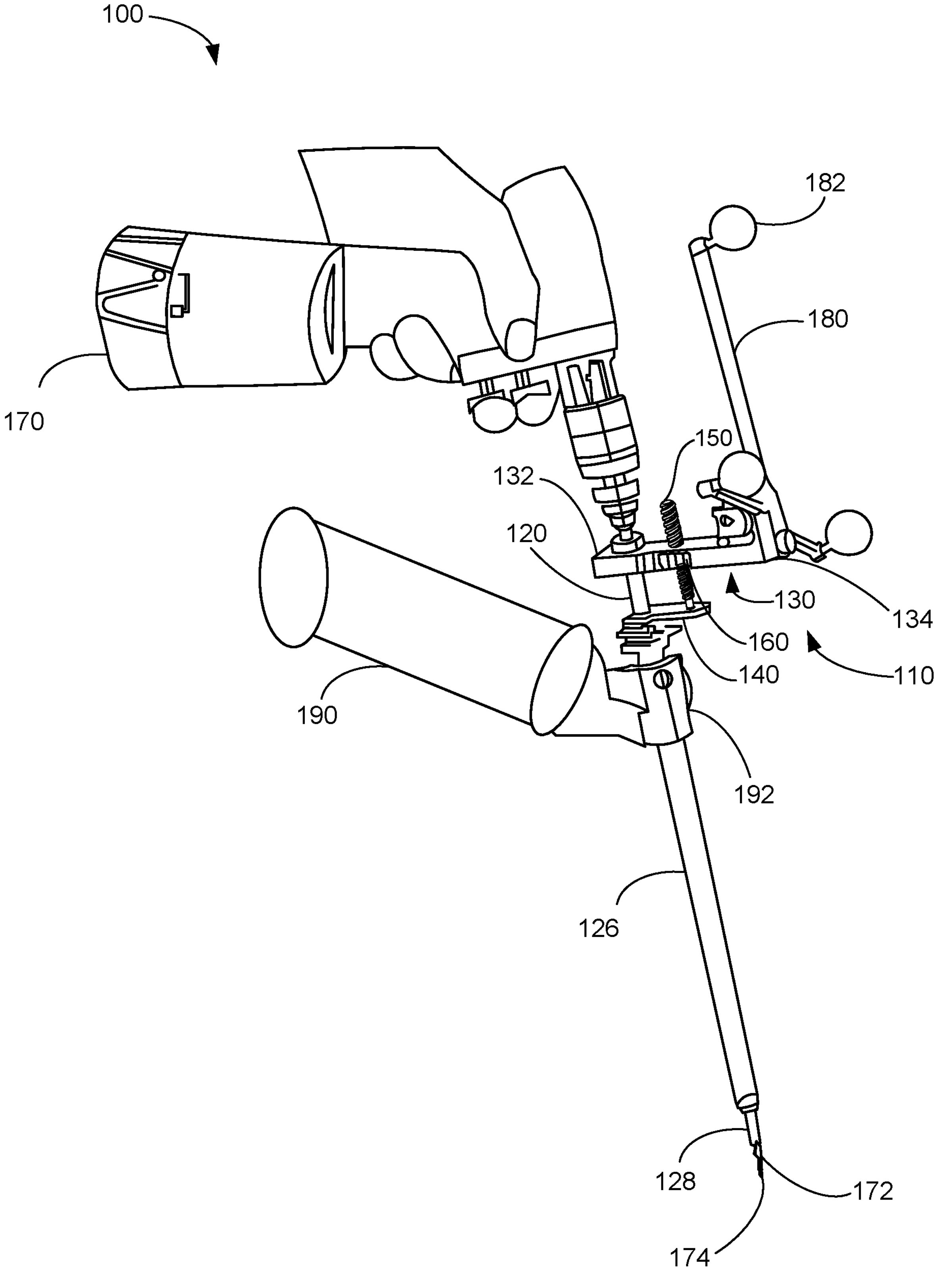
FIG. 1 is a view of an example of a system including a depth stop adapter attached to a drill and a navigational array.

In furtherance of the brief description provided above and associated textual detail of each of the figures, the following description provides additional details of example embodiments.

Detailed illustrative examples are disclosed herein. However, specific functional details disclosed herein are merely representative for purposes of describing example embodiments. Examples may, however, be embodied in many alternate forms and should not be construed as limited to only the embodiments set forth herein.

Accordingly, while examples are capable of various modifications and alternative forms, embodiments are shown by way of example in the drawings and will herein be described in detail. It should be understood, however, that there is no intent to limit examples to the particular forms disclosed. To the contrary, examples are to cover all modifications, equivalents, and alternatives falling within the scope of examples.

It will be understood that, although the terms first, second, etc. may be used herein to describe various elements, steps, and/or calculations, these elements, steps, and/or calculations should not be limited by these terms. These terms are only used to distinguish one element, step, and/or calculation from another. For example, a first calculation could be termed a second calculation, and, similarly, a second step could be termed a first step, without departing from the scope of this disclosure. As used herein, the term "and/or" and the "/" symbol includes any and all combinations of one or more of the associated listed items.

As used herein, the singular forms "a", "an" and "the" are intended to include the plural forms as well, unless the context clearly indicates otherwise. It will be further understood that the terms "comprises." "comprising," "includes" and/or "including," when used herein, specify the presence of stated features, integers, steps, operations, elements, and/or components, but do not preclude the presence or addition of one or more other features, integers, steps, operations, elements, components, and/or groups thereof. Therefore, the terminology used herein is for the purpose of describing particular embodiments only and is not intended to be limiting of example embodiments.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Herein, example embodiments of the present disclosure will be described in detail. Example embodiments of the present disclosure provide a vial adapter, system, and method as described below.

FIG. 1 is a view of an example of a system 100 including a depth stop adapter 110 attached to a surgical drill 170 (e.g., or any power tool) and a navigational array 180. The depth stop adapter 110 may include a depth stop guide tube 120, a housing 130, a foot plate 140, a rod 150, and a depth control element 160. The surgical drill 170 can be removably inserted through the depth adapter 110 by inserting the surgical drill 170 to the depth stop adapter 110. The drill 170 may be inserted through the depth stop adapter 110 proximate a first end 132 of the depth stop adapter 110. The drill 170 has an attached drill bit 172, having a drill bit tip 174, that can extend through a hollow interior of the depth stop guide tube 120. The drill bit tip 174 may extend through an end of the depth stop guide tube 120 opposite the drill (e.g., a bottom end of the robot guide tube 192) as shown in FIG. 1 for use in surgery.

The navigational array 180 may be attached to the depth stop adapter 110. For example, the navigational array 180 may be attached to the depth stop adapter 110 proximate a second end 134 of the depth stop adapter 110. The navigational array 180 may include tracking elements 182. Tracking elements may include one or more of light emitting diodes (LEDs), ultrasonic emitters, electromagnetic field emitters, and/or passive tracking elements.

The system 100 may include a robot arm 190 for the surgeon to use during surgery to stabilize the system 100 during surgery. The robot arm 190 may be detachably connected to the depth stop guide tube 120 by for example a robot guide tube 192 or other suitable linking structure that is connected to (e.g., clamped) to the depth stop guide tube 120. The robot guide tube 192 may be secured by a robot arm 190 or may alternatively be secured manually by the surgeon.

The robot arm 190 and/or robot guide tube 192 may hold the sleeve 126. A drill guide 128 may be inserted into and/or attached to the sleeve 126. The depth stop adapter 110 may be attached to the drill 170 such that the housing 130 does not move along the axis of the drill bit 172. The drill 170 and/or the (e.g., attached) depth stop adapter 110 may be inserted into the sleeve 126 and/or the drill guide 128. Alternatively, the drill guide 128 may be omitted. The drill 170 and/or the (e.g., attached) depth stop 110 adapter may be inserted (e.g., directly) into the sleeve 126.

Figure 2:
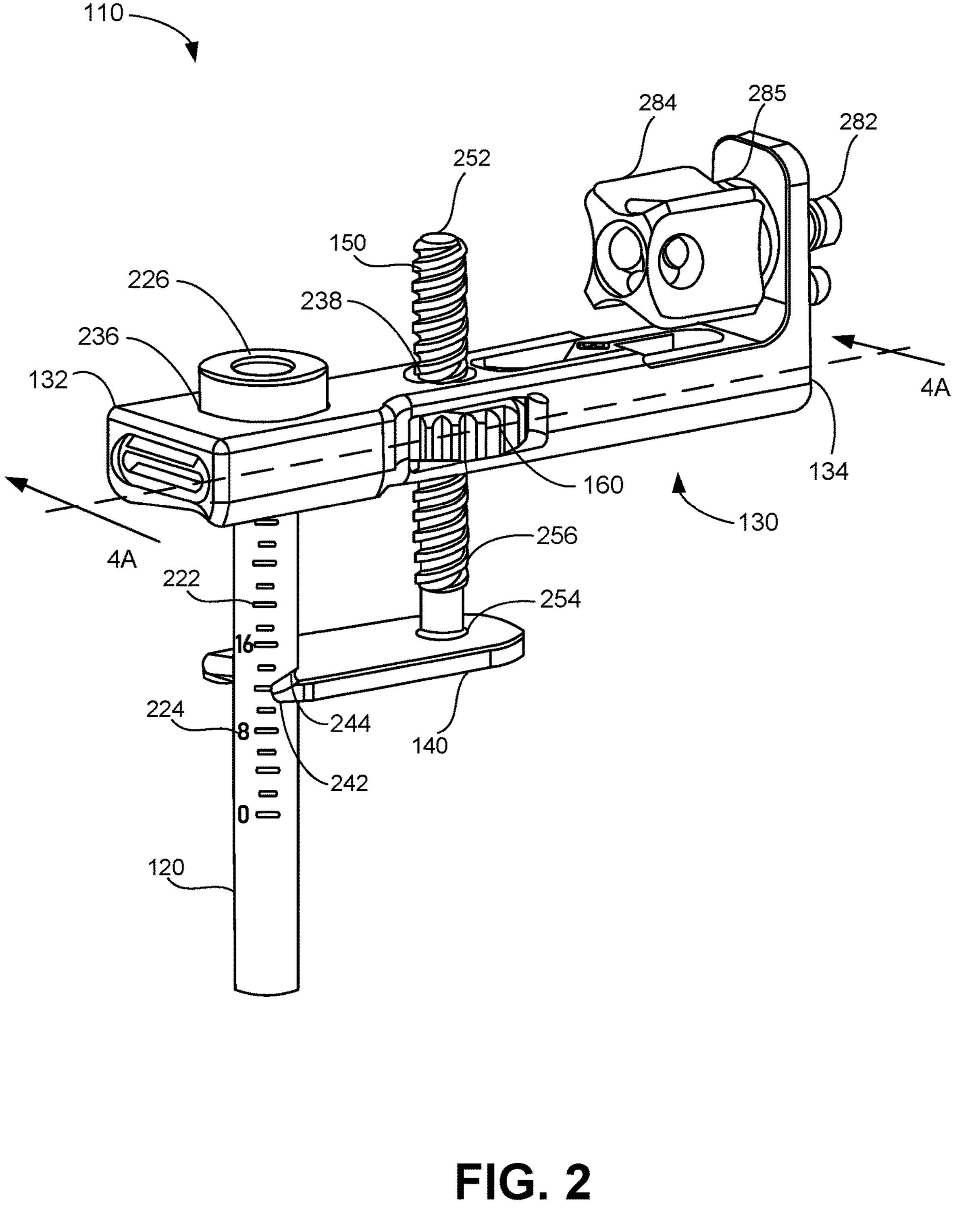
FIG. 2 is a view of a depth stop adapter in accordance with the system of FIG. 1.

FIGS. 2 and 3 are different perspective views of the depth stop adapter 110 of FIG. 1. FIG. 4 is a cross-sectional view of the depth stop adaptor 110 taken along the line 4A-4A of FIG. 1. The depth stop adapter 110 includes a housing 130 with a first end 132 and a second end 134. The first end 132 may be configured for coupling to an instrument, for example a surgical drill and/or a robot. The second end 134 may be configured for coupling to a navigational array 180. The depth stop adaptor 110 may have an attachment mechanism for attaching the navigation array 180 to the depth stop adaptor 110. For example, the attachment mechanism may be a threaded connector 282 with knob 284 that can be coupled to a threaded aperture 285 in the depth stop adapter 110 and a threaded aperture in the navigation array. The knob 284 can be rotated to tighten or loosen to attach the navigational array 180 to the depth stop adaptor 110. The depth stop adapter 110 may cooperate with a sleeve 126 inserted in the robot guide tube 192.

The housing 130 includes a first aperture 236 and/or a second aperture 238 as shown in FIG. 2. The first aperture may be configured to receive the depth stop guide tube 120. For example, a diameter of the first aperture 130 may be sized to fit the depth stop guide tube 120. A cap 226 may attach to the depth stop guide tube 120 and be configured to hold the depth stop guide tube 120 in place relative to the first aperture 236. Alternatively, the cap 226 may be integral with the depth stop guide tube 120. The cap 226 may have a larger diameter than the diameter of the depth stop guide tube 120 as shown in FIG. 4. In this instance, the first aperture 236 may be sized to fit the cap 226. The first aperture 236 may include a first diameter 437 that is proximate the cap 226 and a second diameter 439 distal from the cap 226 as shown in FIG. 4. The first diameter 437 may equal the second diameter 439. The first diameter 437 may be larger than the second diameter 439 and correspond to the cap size so that the cap 226 can rest on the housing that defines the first aperture 130, while the second diameter 439 may correspond to the depth stop guide tube diameter. This may avoid unwanted motion while the depth stop adapter is in use. The depth stop guide tube 120 may be rigidly attached to the housing 130 by for example welding the depth stop guide tube 120 to the housing 130.

The housing 130 includes a second aperture 238. The second aperture may be configured to receive a rod 150 as shown in FIGS. 1-4. The rod 150 may be at least partially threaded 256 as shown in FIG. 2. For example, the rod threads 256 may be one or more of helical, straight, tapered, square, V-shaped, acme, knuckle, buttress, worm, single, multi, Metric standard, British standard, and/or Unified standard threads. The rod includes a proximate end 252 and a distal end 254. A foot plate 140 may be attached to the distal end 254. For example, the foot plate 140 may be detachably connected to the rod 150. Examples of connections may include a form-fit connection, a pin and hole mechanism, and/or a threaded connection. Alternatively, the foot plate 140 may be welded to the rod 150 and/or attached with an adhesive (e.g., glue). The foot plate 140 may rest against the drill guide so that the foot plate 140 is moveable relative to the drill guide.

A depth control element 160 may be disposed, at least partially, within the housing 130 as shown in FIGS. 1-4. Alternatively, the depth control element 160 may be disposed on either side of the housing (e.g., which in such case may be solid) and/or may be secured to the housing in a rotatable manner. The depth control element 160 may be configured to adjust a position of the foot plate 140 relative to the housing 130, for example by rotation. The depth control element 160 may be a wheel having a notched exterior 366, a center aperture 367, and threaded interior 368 as shown in FIG. 3A. The notched exterior 366 may aid a user in gripping and/or turning the depth control element 160. A user can rotate the threaded exterior of the depth control element 160 to cause translational movement of the rod 150 and the foot plate 140. The rod threads mate with the threaded interior of the depth control element 160 in a gearing manner, so that when the depth control element 160 is rotated, the rod 150 moves axially. A position of the rod 150 and the foot plate 140 may be adjusted relative to the housing 130 with movement (e.g., rotation) of the depth control element 160. For example, the rod 150 and the foot plate 140 may move relative to the housing 130 coincidently with movement of the depth control element 160. The rod 150 may move with the foot plate 140 toward or away from the housing 130, for example depending on a direction of rotation of the depth control element 160.

The depth control element 160 may provide tactile feedback. For example, the depth control element 160 may include a textured surface. There may be one or more ridges or notches 362 comprised in the depth control element 160. The ridges 362 may be separated by grooves 364, for example with a spacing between two ridges 362 (e.g., the spacing of one groove) being uniform for the spacing between any adjacent two ridges. Each ridge 362 and/or groove 364 may correspond to a predetermined change in a depth (e.g., position of the foot plate 340).

The depth control element 160 may be laterally offset from the depth stop guide tube 120. For example, the depth control element 160 may be between the depth stop guide tube 120 and a second end 134 of the housing 130. This position may be a natural position for a user's hand to be located. For example, the user may have one hand on a drill and the other hand on the depth stop adapter 110. The depth control element 160 may be positioned such that the user's thumb or pointer finger naturally lands near a position of the depth control element 160. This may result in easy adjustment of the depth, without the need to look (e.g., constantly look) at the depth control element 160 when changing the depth. The user's other hand may be used to hold the drill.

The foot plate 140 and/or the depth stop guide tube 120 may be configured to provide a depth indication. For example, the depth stop guide tube 120 may include indicia 222, 224. Indicia 222, 224 (e.g., particular indicia/marking(s)) may be indicated by the foot plate 140. For example, a bevel 242 of the foot plate 140 may be configured to contact the depth stop guide tube 120 and/or point to the indicia. The bevel 242 may be comprised in a notch 244 configured to at least partially enclose the depth stop guide tube 120. The indicia may include a scale with a plurality of markings 222. Markings 222 may include, for example, one or more lines. Each of the plurality of markings may be associated with a depth measurement. For example, the depth measurements may be associated with a distance that a drill bit extends from the sleeve 126 (e.g., the bottom end).

One or more of the plurality of markings 222 may be labeled. For example, a marking 222 may be labeled with a number 242. The number 242 may be associated with the depth measurement. Additionally, or alternatively, markings 222 may include different lengths. Each length may be associated with an increment. For example, there may be three marking lengths. A first marking length may be associated with a ten millimeter increment, a second marking length may be associated with a five millimeter increment, and/or a third marking length may be associated with a one millimeter increment. Additionally, or alternatively, one or more marking lengths may be associated with a fraction of a distance unit, for example of a standard distance unit. A standard distance unit may include a millimeter, a centimeter, an inch, or multiple units of measurement. Marking lengths may be associated with length increments. For example, a longest marking length may be associated with a largest measurement (e.g., one centimeter and/or one inch) and a smallest marking length may be associated with a smallest measurement (e.g., one millimeter, two millimeters, and/or one sixteenth inch). Intermediate measurements may be associated with corresponding marking length increments.

Figure 3A:
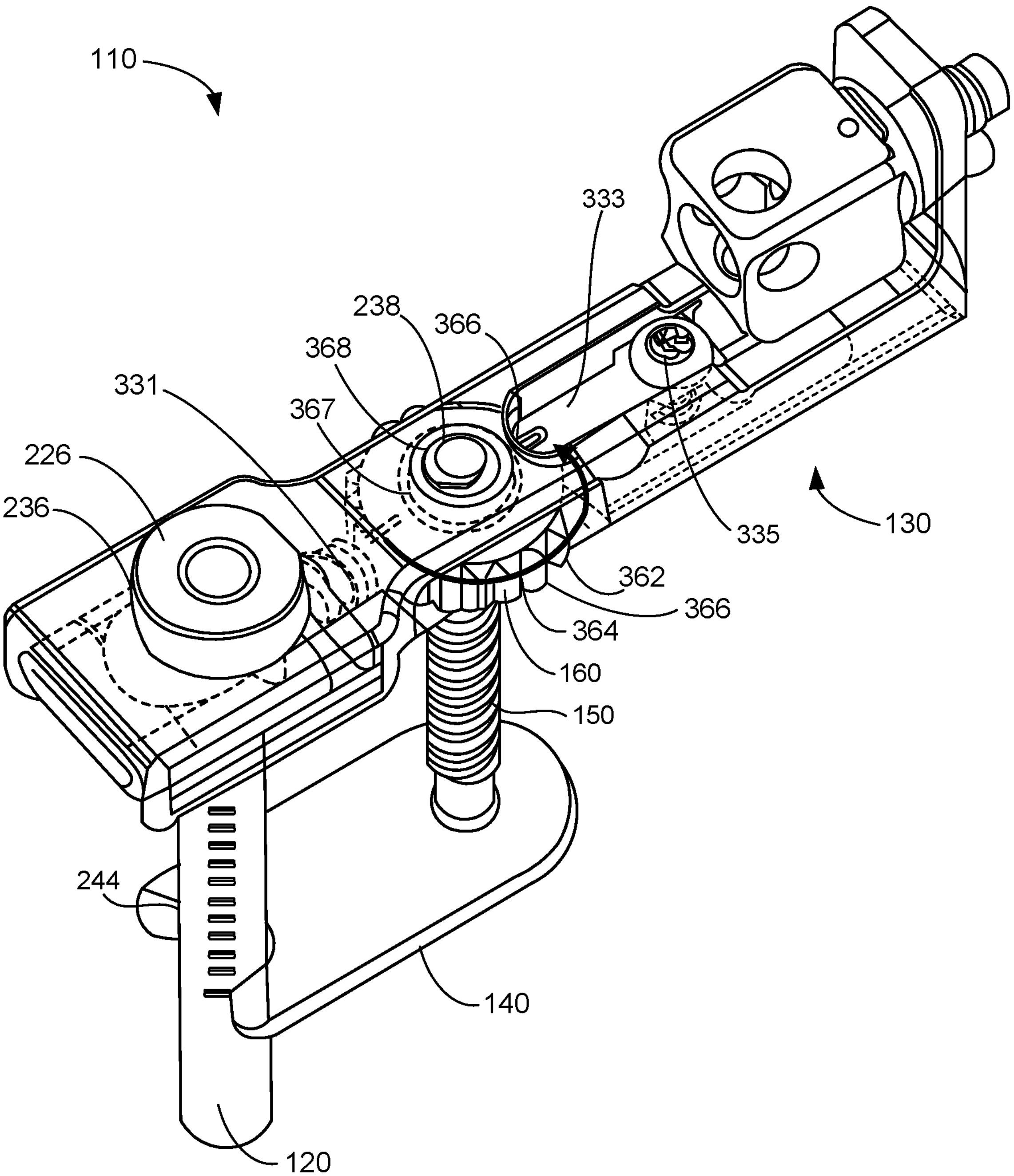
FIG. 3A is another view of the depth stop adapter of FIG. 1.
Figure 3B:
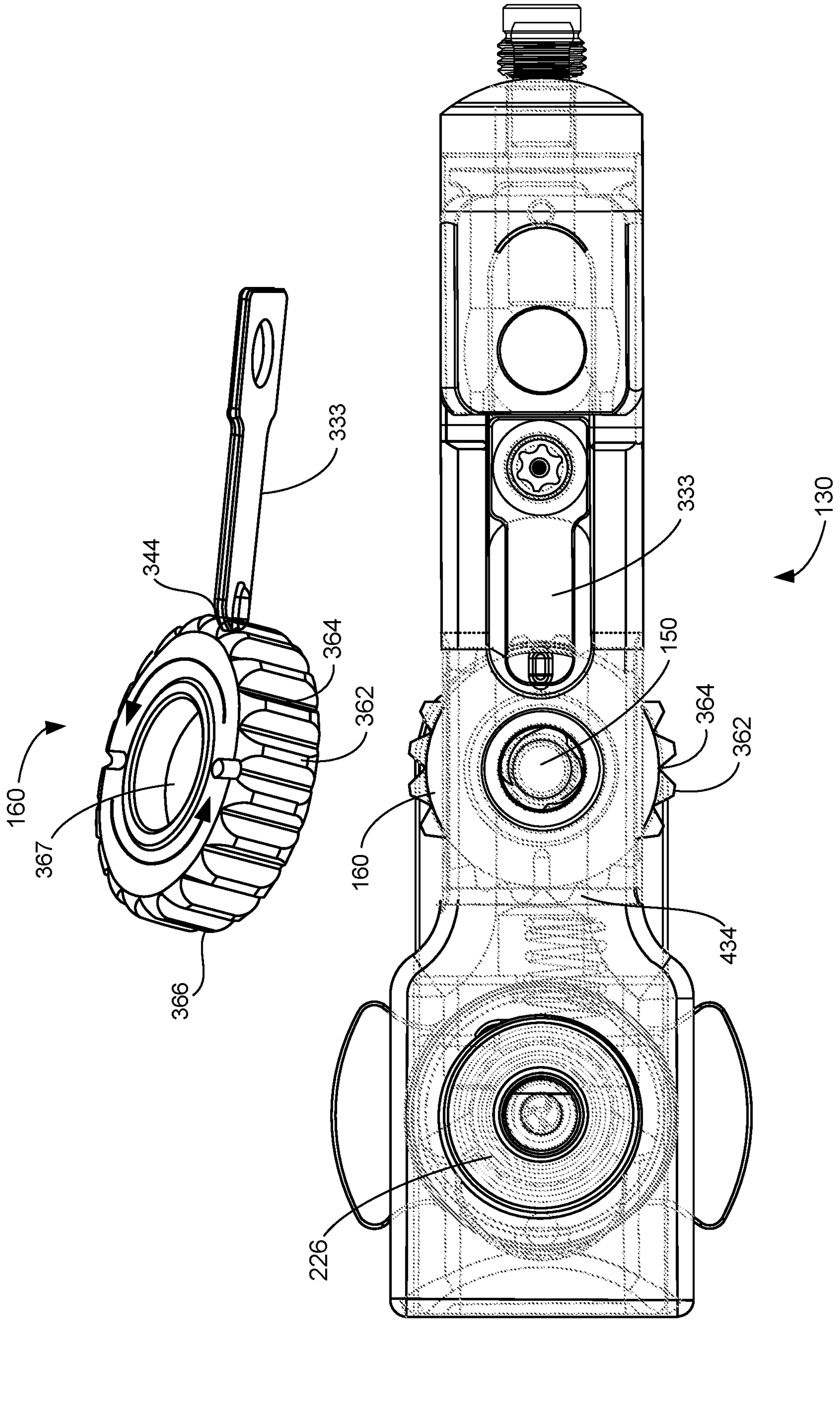
FIG. 3B is another view of the depth stop adapter of FIG. 1.
Figure 4:
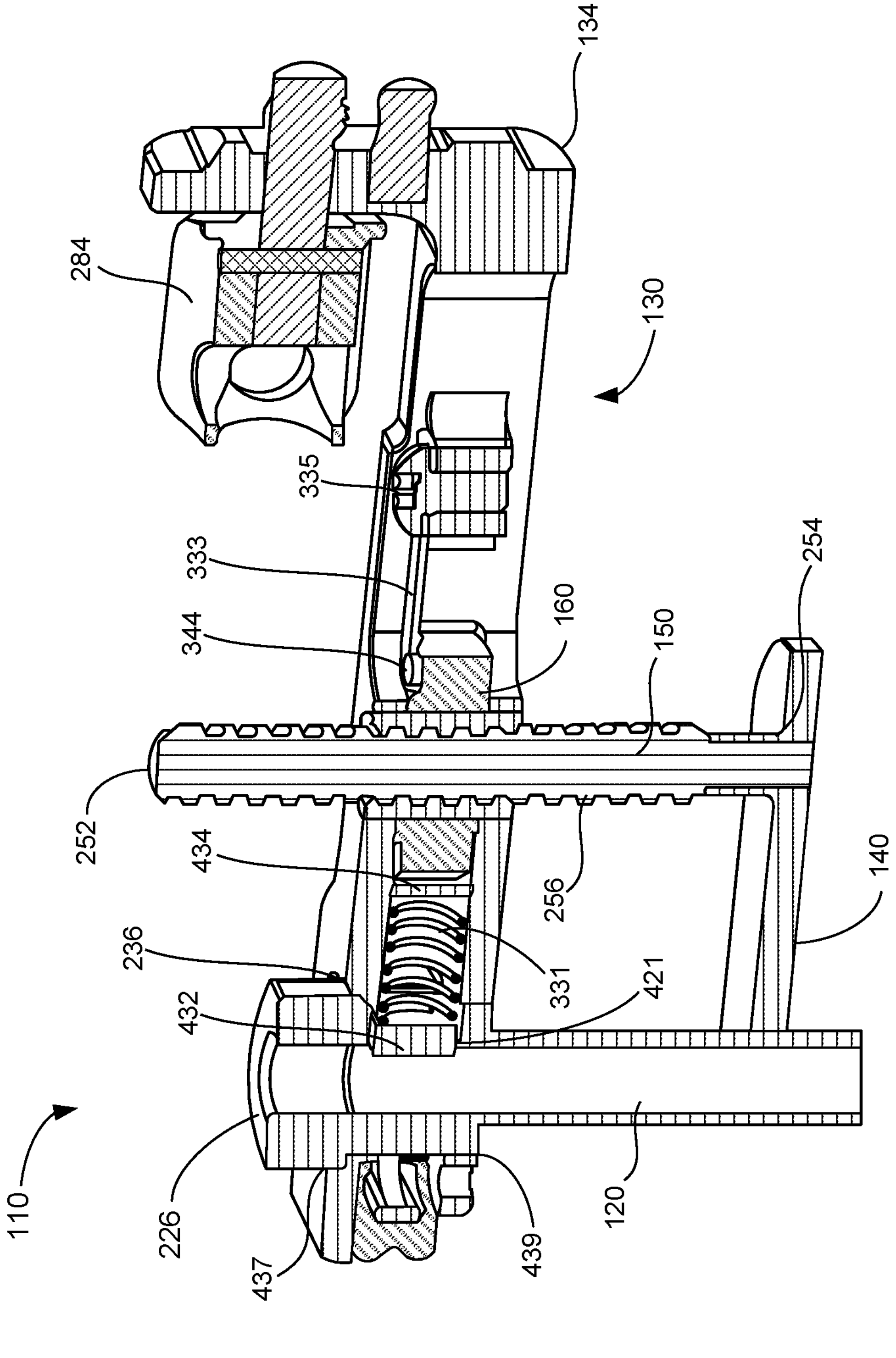
FIG. 4 is a sectional view of an example depth stop adapter in accordance with the system of FIG. 1 taken along line 4A-4A of FIG. 2.

As shown in FIG. 3A, FIG. 3B, and FIG. 4, a sensory feedback element 333 may be included in the housing 130. The sensory feedback element 333 may be a leaf spring having a rounded element 344 proximate one end. Alternatively, the sensory feedback element 333 may be a ball bearing, a ball detent, and/or a spring element (e.g., other type of spring). The sensory feedback element 333 may interface with the depth control element 160. For example, the rounded element 344 of the sensory feedback element 333 may be disposed in a groove 364 between two ridges 362 of the depth control element 160. The sensory feedback element 333 may be attached to a fastener 335, for example at an end opposite the rounded element 344. Attachment at the fastener 335 may be a fixed position, which may result in sensory feedback with movement of the depth control element 160 (e.g., by a predetermined amount).

Sensory feedback may be produced by the sensory feedback element 333. For example, sensory feedback may be produced when the sensory feedback element 333 snaps into and/or out of a groove 364 of the depth control element 150. The sensory feedback element 333 may snap into a groove 364 when the depth control element 160 is rotated. For example, the sensory feedback may include an audible click when the rounded element 344 of the sensory element 333 moves out of a groove 364, is compressed by a ridge 362, and slides into another groove 364 with rotation of the depth control element 160. Rotation of the depth control element 160 is indicated by arrows. For example, FIG. 3B shows the rounded element 344 of the sensory feedback element 333 with the depth control element 160. When the depth control element 160 is rotated, the sensory feedback element 333 may compress and expand. The sensory feedback element 333 may compress when contacting a ridge 362. The sensory feedback element 333 may expand when snapping into a groove 364. The audible click may be caused by the sensory feedback element 333 expanding and/or snapping into a groove 364. The audible click may correspond to a predetermined change in the position of the foot plate 140 defined by the number of groves 364, the size of the grooves 364, and the diameter of the depth control element 160. Audible feedback may make it unnecessary for a user of the system to look at the indicia, for example in order to determine the depth of a drill bit. For example, the audible click may correspond to a 2 mm change in the position of the foot plate 140. Therefore, a user may know that the depth of the drill bit has changed by 2 mm for each audible click. Each audible click may correspond to a predetermined rotation of the depth control element 160. For example, an audible click may correspond to 15 degrees or 180 degrees of rotation of the depth control element 160. The surgeon may associate each audible click with the predetermined change in the position of the foot plate 140 and/or the depth of the drill bit. The sensory feedback element 333 may additionally, or alternatively, snap to a ridge 362 (e.g., each ridge).

It will be appreciated that the predetermined change and audible click can be set based on the geometry and the size of the components (e.g., the spring characteristics of the leaf spring). The sensory feedback element 333 may be configured to limit (e.g., rotational) movement of the depth control element 160. For example, the sensory feedback element 160 may include a slot 366. The slot 366 and sensory feedback element 333 may provide pressure, which limits movement of the depth control element 160. A predetermined pressure applied to the depth control element 160 may move the depth control element 160. The sensory feedback element 333 may be removably attached to the housing, for example with a fastener 335. The fastener may be any type of fastener, for example a screw, a bolt, and/or a rivet. Alternatively, the sensory feedback element and/or the fastener may be welded to the housing 130.

An elastic element 331 may be disposed in the housing 130. For example, the elastic element 331 may be a spring. The elastic element 331 may be in contact with a separator 434. The separator 434 may avoid contact of the elastic element 331 and the depth control element 160. Block 432 is disposed proximate one end of the elastic element 331 and is configured to contact the depth stop guide tube 120. The elastic element 331 may apply a force (e.g., stored energy) to block 432, so that the block 432 is pushed against the depth stop guide tube 120, which for example may facilitate connection to the drill. By compressing the spring 331 and moving the block 432 away from the depth stop guide tube 120, the depth stop guide tube 120 can be removed for so that the depth stop adapter 120 can be cleaned. Alternatively, the depth stop guide tube 120 may be welded to the housing 130. One or more holes may be included in the housing 130 and/or depth stop guide tube 120, for example to facilitate cleaning. Alternatively, or additionally, an opening 421 may be included in the depth stop guide tube 120. The block 432 may be configured to enter the opening 421, for example when the elastic element 331 applies a force (e.g., stored energy) to the block 432. The block 432 may contact and/or facilitate connection to the drill.

Figure 5A:
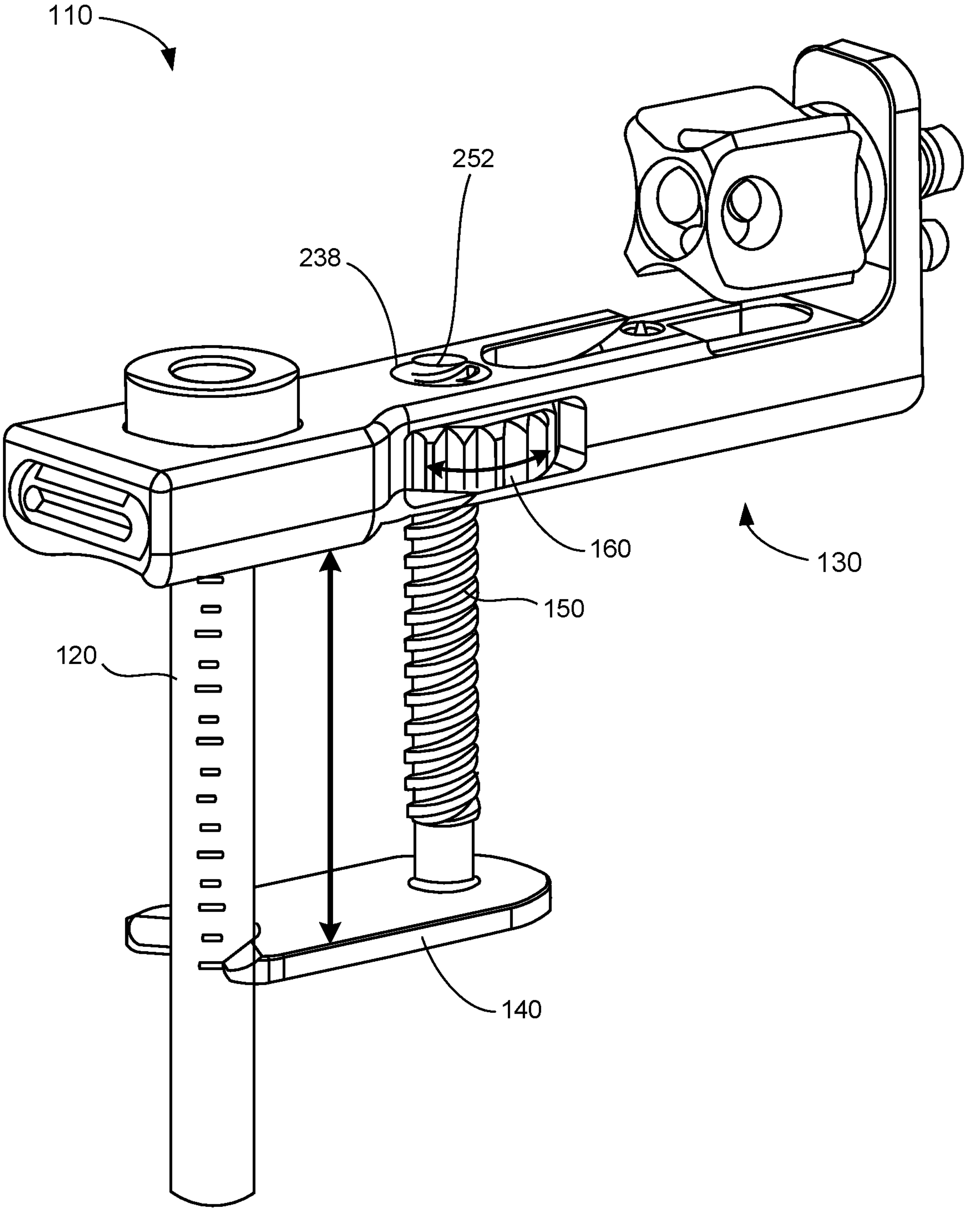
FIG. 5A is a view of the depth stop adapter of FIG. 1 in a first position.
Figure 6A:
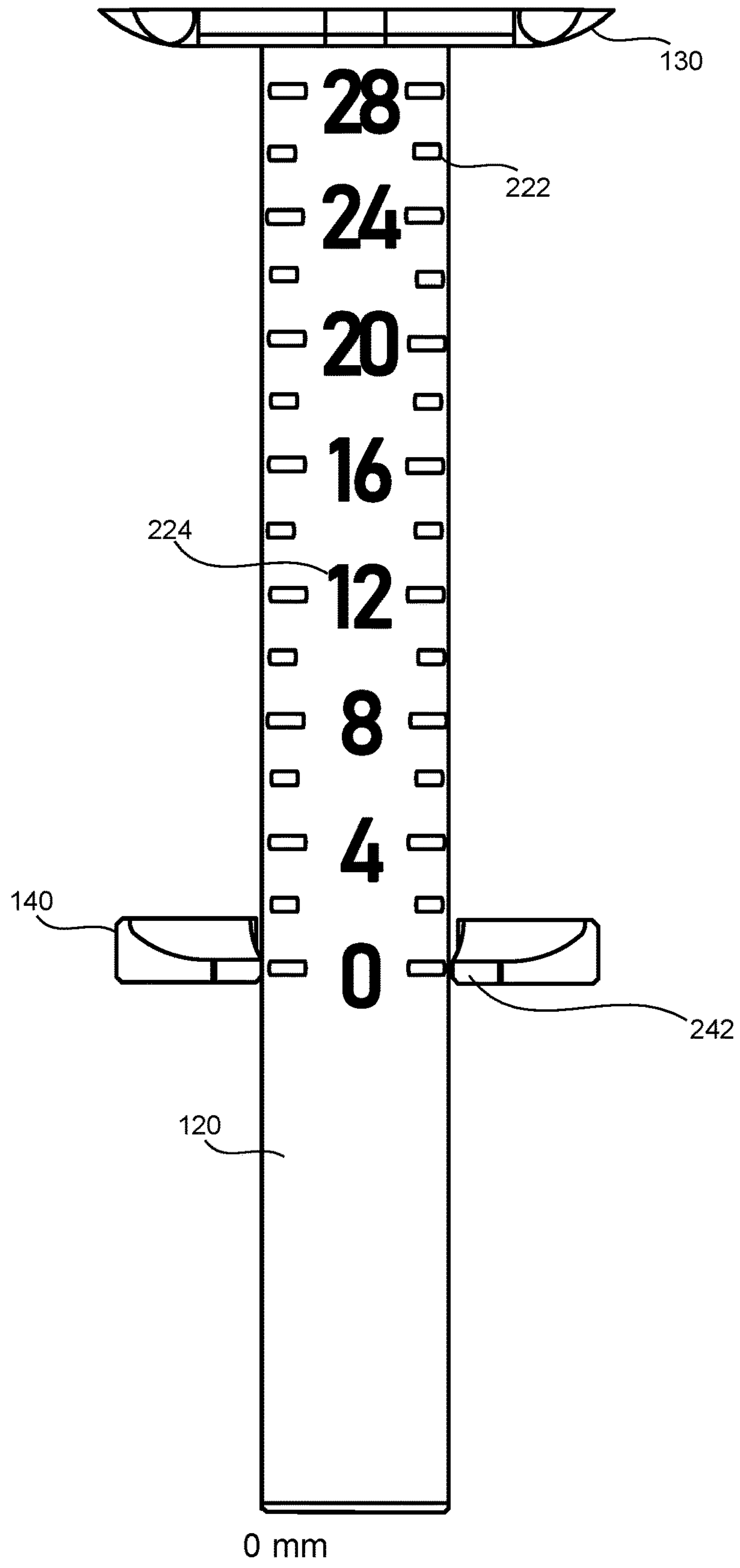
FIG. 6A is a view of an example depth stop guide tube of the depth stop adapter of FIG. 1 in a first position.

FIG. 5A and FIG. 6A are views of an example depth stop adapter 110 and the foot plate 140 in a first position. The first position may be an initial position. The initial position may correspond to a depth of 0 mm. In the first position, the foot plate 140 is positioned furthest from a housing 130. The proximate end 252 of the rod 150 may be nearest a second aperture 238 of the housing 130 in the first position. The proximate end 252 may be configured to stop further movement of the distal end 254 of the rod 150 away from the housing 130. The depth stop guide tube 120 may have a fixed position relative to the housing 130.

The depth control element 160 may be configured to rotate such that the foot plate 140 position changes with rotation of the depth control element 160. For example, the rod 150 may be configured to contact the depth control element 160. When the depth control element 160 rotates, the rod 150 may move away from and/or toward the housing 130, for example depending on a direction of rotation of the depth control element 160. The foot plate 140 may prevent rotation of the rod 150. Movement of the rod 150 may cause the foot plate 140 to move toward or away from the housing 130. The rod 150 may contact the depth control element 160 at an inner portion of the depth control element 160. Additionally, or alternatively, the rod 150 may contact the depth control element 160 at one or more grooves 364 and/or ridges 362. The rod 150 may be a threaded rod. For example, a thread may be one or more of helical, straight, tapered, square, V-shaped, acme, knuckle, buttress, worm, single, multi, Metric standard, British standard, and/or Unified standard.

Figure 5B:
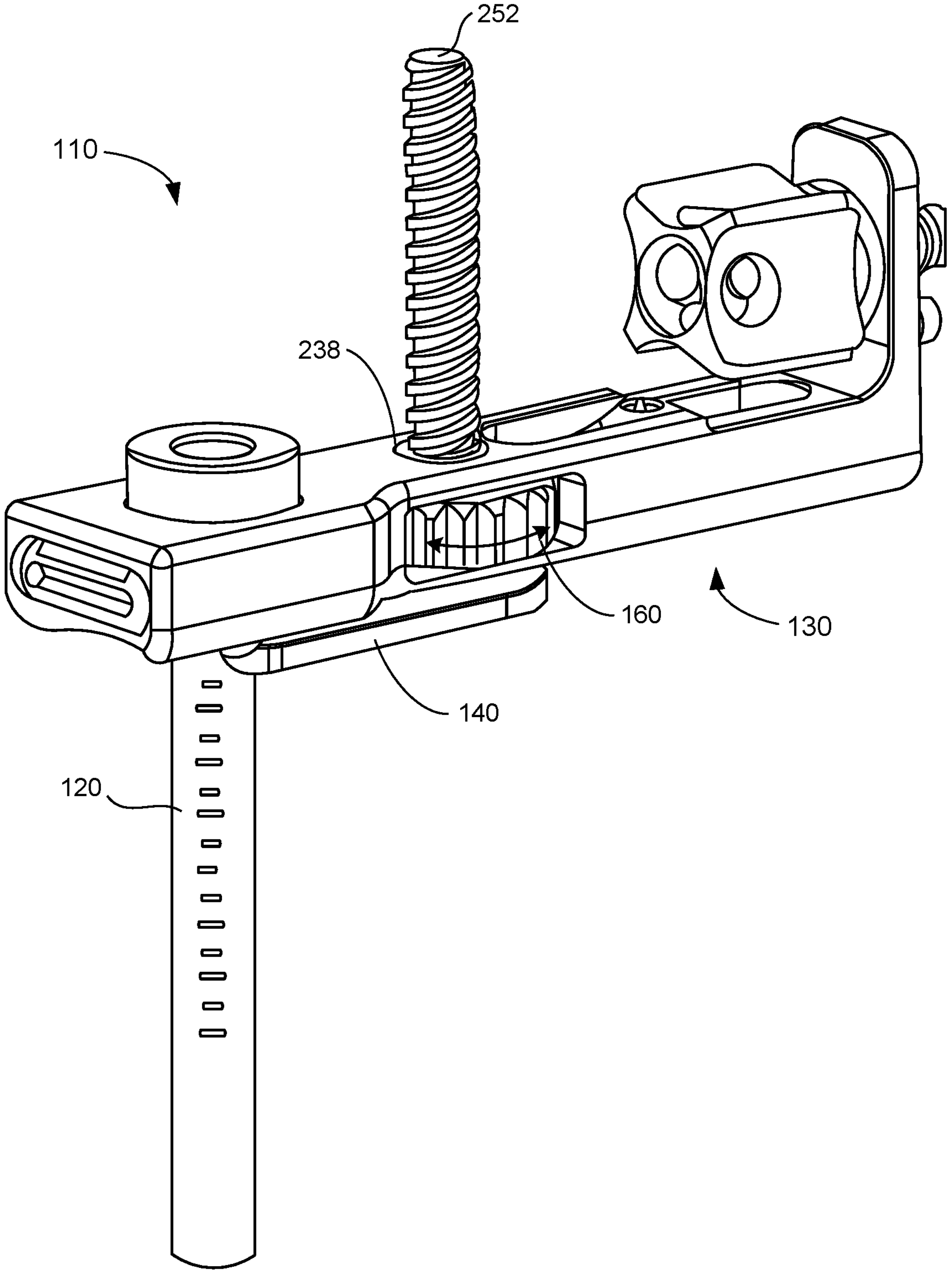
FIG. 5B is a view of the depth stop adapter of FIG. 1 in a second position.
Figure 6B:
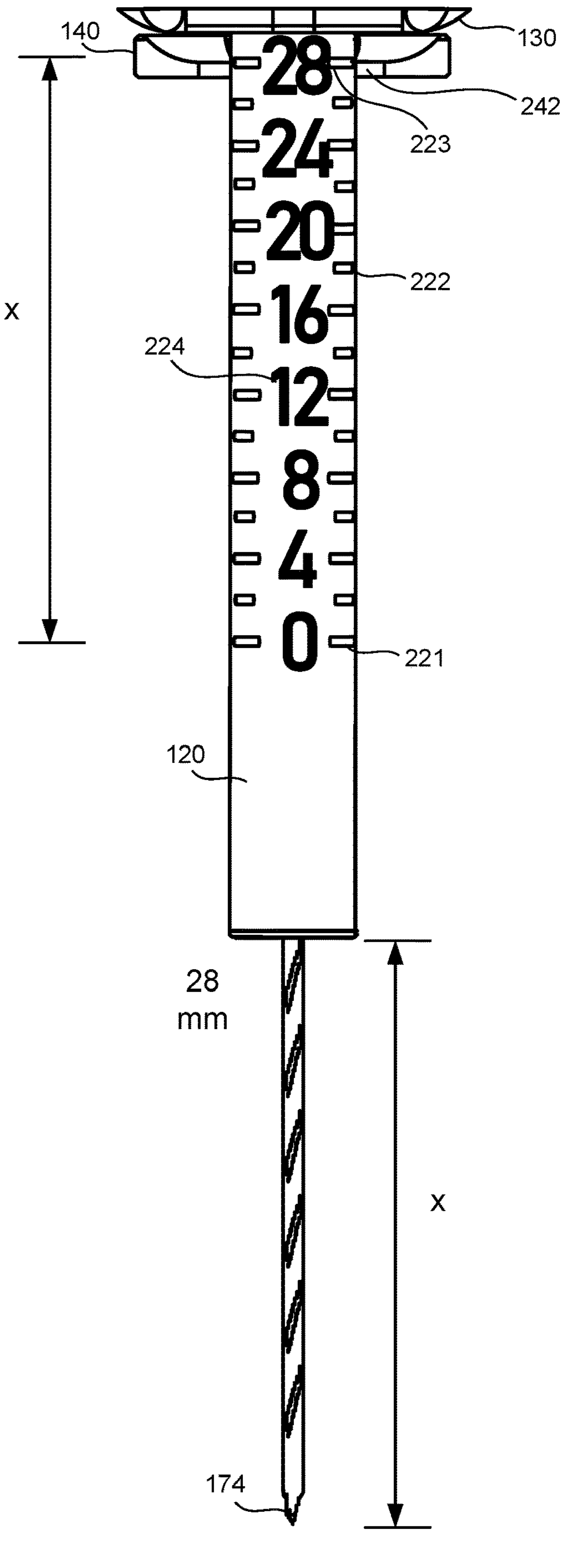
FIG. 6B is a view of the example depth stop guide tube of FIG. 6A in a second position.

FIG. 5B and FIG. 6B are views of an example depth stop adapter 110 in a second position. The second position may correspond to a depth of 28 mm. The foot plate 140 may be at a position closest to (e.g., abutting) the housing 130. The rod 150 attached to the foot plate 140 may include a proximate end 252. The proximate end may be furthest from a second aperture 238 of the housing 130 in the second position. The depth stop guide tube 120 may have a fixed position relative to the housing 130. As shown, when the foot plate 140 is moved from the first position in FIG. 5A to the second position in FIG. 5B the rod 150 moves transversely to the housing when the depth control adapter is rotated, which causes movement of the foot plate 140 relative to the depth stop guide tube 120 to show the drill guide position based on the drill guide indicia.

FIGS. 6A and 6B show the depth stop guide tube 120 include indicia 222, 224. Indicia 222, 224 (e.g., particular indicia/marking(s)) may be indicated by the foot plate 140. For example, a bevel 242 of the foot plate 140 may be configured to contact the depth stop guide tube 120 and/or point to the indicia. The bevel 242 may have a thickness sized to correspond to the indicia. The indicia may include a scale with a plurality of markings 222. Markings 222 may include, for example, one or more lines. Each of the plurality of markings may be associated with a depth measurement. For example, the depth measurements may be associated with a distance that a drill bit 174 extends from the depth stop guide tube 120 (e.g., the bottom end of the guide tube). The distance that the drill bit 174 extends from the depth stop guide tube 120 may correspond to a drilling depth, for example into bone.

One or more of the plurality of markings 222 may be labeled. For example, a marking 222 may be labeled with a number 242. The number 242 may be associated with the depth measurement. Additionally, or alternatively, markings 222 may include different lengths. Each length may be associated with an increment. For example, a longest marking length may be associated with a largest measurement (e.g., one centimeter and/or one inch) and a smallest marking length may be associated with a smallest measurement (e.g., one millimeter and/or one sixteenth inch). Intermediate measurements may be associated with corresponding marking length increments.

The indicia may be on an inner surface of the depth stop guide tube 120, for example on an inner surface of the outer sleeve. Additionally, or alternatively, the indicia may be on an inner and/or outer surface of the inner sleeve. For example, the outer sleeve and/or inner sleeve may be transparent, and indicia may be visible when viewed from the ambient environment.

The depth control element may be configured to rotate such that the foot plate 140 position changes with rotation of the depth control element. For example, when the depth control element 160 rotates, the foot plate 140 may move toward or away from the housing 130. Movement of the foot plate 140 toward or away from the housing 130 may depend on the movement direction of the depth control element. For example, a clockwise movement of the depth control element may result in movement of the foot plate 140 toward the housing 130 (e.g., an increased depth). Counter-clockwise movement of the depth control element 160 may result in movement of the foot plate 140 away from the housing 130 (e.g., a decreased depth).

FIG. 6B shows a drill bit 174 at an example depth (e.g., x). The example depth (e.g., x) may equal a depth indicated by one or more markings 222, the foot plate 140, and/or the bevel 242. For example, the depth that the drill bit 174 extends from the depth stop guide tube 120 (e.g., x) may equal a distance between a first (e.g., lowest) marking 221 and a second marking 223 indicated by the foot plate 140 and/or the bevel 242. The depth of the drill bit may correspond to the indicia 224 that corresponds to the marking 222 indicated by the foot plate 140 and/or the bevel 242.

Figure 7:
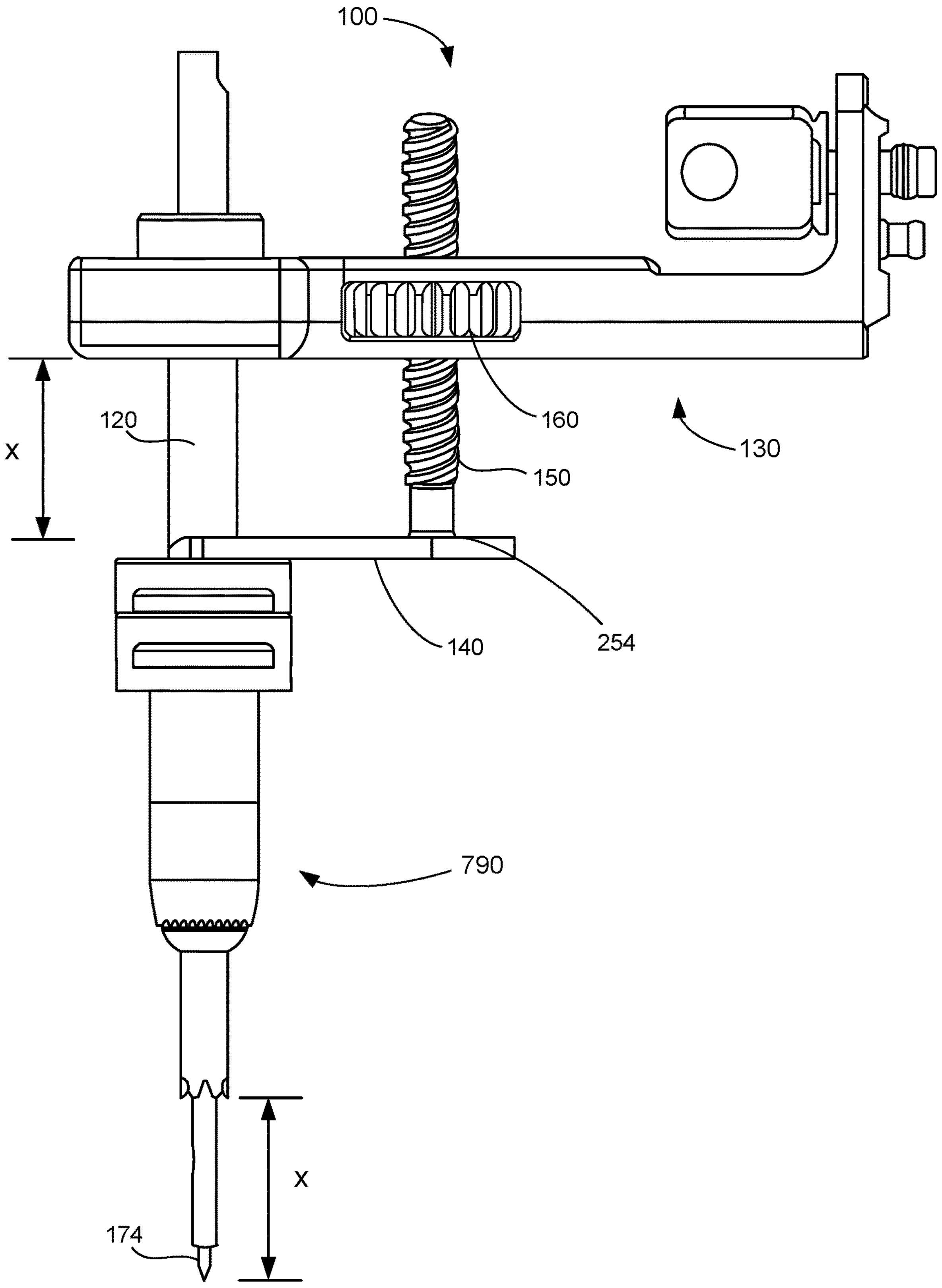
FIG. 7 is view of an example of a system including the depth stop adapter of FIG. 1 with a drill bit at an example depth.

FIG. 7 is view of an example of a system 100 including a depth stop adapter 110 with a drill bit at an example depth (e.g., x). Housing 130 is attached to rod 150 and depth stop guide tube 120. The rod 150 is attached to a foot plate 140 at a distal end 254. The foot plate may be configured to move a access guide 790. For example, the foot plate 140 may be connected to the access guide 790 such that the access guide 790 moves away from or toward the housing 130 with movement of the foot plate 140. As the access guide 790 moves toward the housing 130, a drill bit 174 extends or extends further from an end (e.g., a bottom end) of the access guide 790 and/or depth stop guide tube 120.

Movement of depth control element 160 correspondingly moves the position of the rod 150, foot plate 140, and/or access guide 790 relative to the housing 130. For example, clockwise movement of the depth control element 160 may result in movement of the rod 150, foot plate 140, and/or access guide 790 toward to the housing 130. This may result in an increased depth of the drill bit 174. Counter-clockwise movement of the depth control element 160 may result in movement of the rod 150, foot plate 140, and/or access guide 790 away from the housing 130. This may result in a decreased depth of the drill bit 174.

It should be emphasized that the above-described embodiments of the present disclosure, particularly, any detailed discussion of particular examples are merely possible examples of implementations and are set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

What is claimed is:

1. A depth stop adapter comprising:
- a depth stop guide tube that defines a hollow interior configured to receive a drill bit such that the drill bit can extend through the depth stop guide tube;
- a housing comprising:
  - a first end and a second end;
  - a first aperture proximate the first end, the first aperture configured to receive the depth stop guide tube; and
  - a second aperture between the first aperture and the second end;
- a foot plate configured to provide a depth indication;
- a rod configured to be received by the second aperture, the rod comprising a proximate end and a distal end, the distal end configured to attach to a foot plate; and
- a depth control element configured to adjust a position of the foot plate relative to the housing.

2. The depth stop adapter of claim 1, wherein the depth control element comprises a wheel configured to rotate such that the foot plate position changes with rotation of the wheel.

3. The depth stop adapter of claim 2, wherein the wheel is attached to a sensory feedback element, the sensory feedback element configured to produce sensory feedback.

4. The depth stop adapter of claim 3, wherein the sensory feedback comprises an audible click and the audible click corresponds to a predetermined change in the position of the foot plate.

5. The depth stop adapter of claim 4, wherein the audible click corresponds to a 180 degree rotation of the wheel.

6. The depth stop adapter of claim 4, wherein the predetermined change in the position of the foot plate is 2 millimeters.

7. The depth stop adapter of claim 3, wherein the sensory feedback element is configured to limit rotational movement of the wheel.

8. The depth stop adapter of claim 3, wherein the sensory feedback element is a leaf spring.

9. The depth stop adapter of claim 3, wherein the wheel comprises a slot, the sensory feedback element configured to connect into the slot.

10. The depth stop adapter of claim 1, wherein the depth stop guide tube comprises indicia associated with a distance that the drill bit extends from a bottom end of the depth stop guide tube.

11. The depth stop adapter of claim 2, wherein the wheel is laterally offset from the depth stop guide tube.

12. The depth stop adapter of claim 1, wherein the foot plate comprises a notch, the notch configured to at least partially enclose the depth stop guide tube.

13. The depth stop adapter of claim 12, wherein the notch further comprises a bevel configured to contact the depth stop guide tube.

14. The depth stop adapter of claim 13, wherein the bevel is configured to indicate a depth by pointing to indicia on the depth stop guide tube, the indicia associated with a distance that the drill bit extends from the depth stop guide tube.

15. The depth stop adapter of claim 1, wherein the depth stop guide tube comprises an outer sleeve and an inner sleeve.

16. The depth stop adapter of claim 15, wherein the inner sleeve comprises a bottom end, the bottom end comprises a beveled tip.

17. The depth stop adapter of claim 2, wherein the rod is a threaded rod and is configured to contact an inner portion of the wheel.

18. The depth stop adapter of claim 2, wherein the foot plate is configured to move toward or away from the housing with rotation of the wheel.

19. The depth stop adapter of claim 1, wherein the second end is configured to attach to a navigational array.

20. A system comprising:
- a depth stop adapter comprising:
  - a depth stop guide tube that defines a hollow interior configured to receive a drill bit such that the drill bit can extend through the depth stop guide tube;
  - a housing comprising:
    - a first end and a second end;
    - a first aperture proximate the first end, the first aperture configured to receive a depth stop guide tube that defines a hollow interior configured to receive a drill bit such that the drill bit can extend through the depth stop guide tube; and
    - a second aperture between the first aperture and the second end;
  - a foot plate configured to provide a depth indication;
  - a rod configured to be received by the second aperture, the rod comprising a proximate end and a distal end, the distal end configured to attach to a foot plate; and
  - a depth control element configured to adjust a position of the foot plate relative to the housing; and
- a robot arm attached to the depth stop adapter.

* * * * *